United States Patent [19]

Workman

[11] Patent Number: 5,610,186

[45] Date of Patent: Mar. 11, 1997

[54] FLEA KILLER METHOD AND COMPOSITIONS

[76] Inventor: Lester J. Workman, P.O. Box 5547, Sarasota, Fla. 34277

[21] Appl. No.: 41,060

[22] Filed: Mar. 31, 1993

[51] Int. Cl.$^6$ .......................... A01N 37/02; A01N 37/06; A01N 65/00

[52] U.S. Cl. .......................... 514/547; 514/529; 514/558; 514/560; 424/195.1

[58] Field of Search .................................. 514/558, 560, 514/529, 547, 711

[56] References Cited

U.S. PATENT DOCUMENTS

| | | | |
|---|---|---|---|
| 4,731,379 | 3/1988 | Panzer | 424/DIG. 10 |
| 4,870,102 | 9/1989 | Puritch et al. | 514/560 |
| 4,919,838 | 4/1990 | Tibbetts et al. | 510/120 |
| 5,017,615 | 5/1991 | Workman | 514/560 |
| 5,030,658 | 7/1991 | Salloum et al. | 514/560 |
| 5,093,124 | 3/1992 | Kulenkampff | 424/195.1 |
| 5,283,259 | 2/1994 | Mather | 514/558 |

*Primary Examiner*—John Pak
*Attorney, Agent, or Firm*—Cushman Darby & Cushman IP Group of Pillsbury Madison & Sutro, LLP

[57] ABSTRACT

A safer, more effective, ectoparasite killer composition consisting essentially of an effective amount of a natural soap, a surfactant, and water.

3 Claims, No Drawings

FLEA KILLER METHOD AND COMPOSITIONS

BACKGROUND OF THE INVENTION

The present invention relates to improved insecticidal compositions for the control of ectoparasites, such as fleas, on domestic animals, i.e., dogs and cats.

Various washes and shampoos have been proposed in the art for controlling ectoparasites, such as fleas, on domestic animals. However, the prior art has not disclosed an insecticidal composition which is effective in controlling fleas on domestic animals without entailing significant disadvantages. These disadvantages include detrimental side effects to the host, including allergic sensitivity reactions as evidenced by the animals's skin and/or fur and difficulty in use (for example, lengthy soak times to enhance the effectiveness of the insecticidal composition).

A series of experiments conducted by the United States government has determined that a number of chemicals, i.e., BHC (benzene hexachloride), chlordane, dinitro ortho-cresol, DDT (dichlorodiphenyltrichloroethene), diocytlamine, heptachlor, parathion, dinitro butyl phenol, paraoxon and lethane, effectively control fleas on domestic animals. However, all of these chemicals have been found to be extremely harmful to the host.

Further tests have determined that a number of low grade flea killers, i.e., paranitroanisole, capric acid, hendecenoic acid, nonyl alcohol, nonyl phenol, tributyl phosphate, butyl salicylate, amyl salicylate, bromo methyl salicylate, hexyl salicylate and valeraldehyde, among others, affect fleas and are not harmful to the host. However, these chemicals have not been found to be sufficiently effective in the control of fleas.

Among the objects of the present invention is the provision of an insecticidal composition which is suitable for application directly to an animal's body and which will eliminate or effectively control fleas without detrimental side effects to the host.

This invention is an improvement of my invention in U.S. Pat. No. 5,017,615, hereby incorporated by reference.

The foregoing as well further objects of the present invention will be more fully understood from the following description.

SUMMARY OF THE INVENTION

Upon continued experimentation I have discovered that a simple two component composition of natural soap and a surfactant in water is a ectoparasite, such as fleas, killer. This composition is much safer and more effective than previous flea killers. It is so safe it can be used to kill flies to roaches, even sprayed in the presence of food and so effective it kills pests on contact.

Suitable surfactant include any of the synthetic detergents which are readily available in commerce and which are described in the literature; for example, in "Surface Active Agents and Detergents," Volumes 1 and 2 by Schwartz, Perry and Berch. Generally stated, the surface active component of an insecticidal composition of my invention may include a synthetic ionic, nonionic, amphoteric or zwitterionic compound, or a mixture of two or more of these compounds. Preferably, cationic, anionic and/or nonionic compounds are used.

The method of my invention comprises applying to an infested animal tan insecticidally effective amount of a composition of the present invention. The insecticidal composition, which is typically a shampoo or like liquid, is applied to the animal's body while the fur is still dry. The shampoo or equivalent composition is rubbed into the fur until lathering begins. The composition thus applied is allowed to remain in contact with the animal's skin and fur for a period of time to at least control and preferably eradicate the ectoparasites contained thereon. The insecticidal composition is then rinsed off the animal's skin and fur.

Instead of being used as a shampoo, the composition may be suitably diluted and used as a spray on the animal or on furniture, carpets or the like to kill fleas or flea larva.

This invention is for a safer, more effective ectoparasite (flea) killer composition consisting essentially of an effective amount of a natural soap, a surfactant, and water. The preferred surfactant is selected from the group consisting of dioctyl sodium sulfosuccinate, dioctyl calcium sulfosuccinate and sodium 2-ethylhexyl sulfate. The natural soap preferably is selected from the group consisting of saponified tallow, lard, coconut oil, palm oil, palm kernel oil, olive oil, castor oil, babassu oil, vegetable oils, foots from refined vegetable oils, their hydrolyzed products, rosin, tall oil, and mixtures thereof. Preferably the soap is saponified with sodium hydroxide or potassium hydroxide. The preferred ratio of the natural soap to the surfactant on a weight-to-weight basis is from about 1:10 to about 10:1.

In another embodiment this invention is a method to kill ectoparasites, such as fleas, on warm blooded animals comprising of applying the composition of any of the embodiments above to the animal, allowing the applied composition to remain in contact with the animal's fur and skin for a period sufficient to kill the ectoparasites and then removing the composition. Preferably the period of contact is from about 30 seconds to about 5 minutes.

It will be understood that while my invention has been described with respect to eradicating and controlling insect infestations in domestic animals (in particular, fleas on dogs and cats) there are numerous other applications to which the compositions of my invention may be put.

The present invention is illustrated in detail in the following examples. These examples are included for illustrative purposes and should not be considered to limit the present invention.

EXAMPLES

Insecticidal composition are prepared as follows:

Example I

| Compound | Percent by Weight |
| --- | --- |
| Dioctyl Sodium Sulfosuccinate | 10 |
| Natural Soap, e.g. Sodium Palmitate | 10 |
| Water | 80 |

Example II

| Compound | Percent by Weight |
| --- | --- |
| Dioctyl Sodium Sulfosuccinate | 12 |

-continued

| Compound | Percent by Weight |
| --- | --- |
| Undecylenic acid Soap | 12 |
| Water | 76 |

What is claimed is:

1. An insecticidal composition for eliminating or controlling ectoparasites on domestic animals, said composition consisting essentially of from 25 weight percent to 75 weight percent of a coconut oil soap, and a surfactant which is dioctyl sodium sulfosuccinate, and the balance water, wherein the ratio of coconut oil soap to dioctyl sodium sulfosuccinate on a weight-to-weight basis is from about 2:3 to about 3:2.

2. A method to kill ectoparasites on a warm blooded domestic animal comprising applying an effective amount of the composition of claim 1 to said animal, allowing said applied composition to remain in contact with said animal's fur and skin for a period sufficient to kill the ectoparasites and removing said composition.

3. The method of claim 2 wherein said period is from about 30 seconds to about five minutes.

* * * * *